(12) United States Patent
D'Agostino et al.

(10) Patent No.: US 10,864,184 B1
(45) Date of Patent: Dec. 15, 2020

(54) METABOLIC THERAPY FOR WOUND HEALING

(71) Applicant: University of South Florida, Tampa, FL (US)

(72) Inventors: Dominic Paul D'Agostino, Tampa, FL (US); Shannon Kesl, Tampa, FL (US)

(73) Assignee: University of South Florida, Tampa, FL (US)

( * ) Notice: Subject to any disclaimer, the term of this patent is extended or adjusted under 35 U.S.C. 154(b) by 276 days.

(21) Appl. No.: 14/554,172

(22) Filed: Nov. 26, 2014

Related U.S. Application Data

(60) Provisional application No. 61/909,811, filed on Nov. 27, 2013.

(51) Int. Cl.
| | | |
|---|---|---|
| A61K 31/047 | (2006.01) | |
| A61K 31/121 | (2006.01) | |
| A61P 17/02 | (2006.01) | |
| A61K 9/00 | (2006.01) | |
| A61K 31/231 | (2006.01) | |
| A61K 31/19 | (2006.01) | |
| A61K 31/198 | (2006.01) | |
| A61K 31/22 | (2006.01) | |
| A61K 36/889 | (2006.01) | |

(52) U.S. Cl.
CPC .......... *A61K 31/231* (2013.01); *A61K 31/047* (2013.01); *A61K 31/19* (2013.01); *A61K 31/198* (2013.01); *A61K 31/22* (2013.01); *A61K 36/889* (2013.01); *A61P 17/02* (2018.01)

(58) Field of Classification Search
CPC ....... A61P 17/02; A61K 9/0019; A61K 9/005; A61K 9/006; A61K 31/047
See application file for complete search history.

(56) References Cited

U.S. PATENT DOCUMENTS

| | | |
|---|---|---|
| 4,767,746 A | 8/1988 | Catsimpoolas et al. |
| 5,578,576 A | 11/1996 | Leddin |
| 5,858,365 A | 1/1999 | Faller |
| 6,239,176 B1 | 5/2001 | Nudelman et al. |
| 2010/0041751 A1 | 2/2010 | Henderson |
| 2011/0178032 A1 | 7/2011 | Henderson |

FOREIGN PATENT DOCUMENTS

KR   2002032469 A   *   5/2002

OTHER PUBLICATIONS

Lundy et al. (Stroke, 1985, 16, 855-860).*
Sen (Wound Repair Regen., 2009, 17, 1-18).*
Zhai et al. (Phytomedicine, 16, 2009, 669-678) (Year: 2009).*
Nagayam et al. (Journal of Parenteral and Enteral Nutrition, 14, 245-249, 1990) (Year: 1990).*
Puchowicz et al. (Journal of Cerebral Blood Flow and Metabolism, 2008, 28, 1907-1916) (Year: 2008).*
What is the Ketogenic Diet (http://www.theketogenicdiet.org/what-is-the-ketogenic-diet/, Feb. 8, 2012, a PDF with pp. 1-4 provided) (Year: 2012).*
Nagayama, M., Thomford, N.R. and Birkhahn, R.H. (1990), Feeding the Rat Intravenously with Ketone Bodies following Colon Anastomosis. Journal of Parenteral and Enteral Nutrition, 14: 245-249. (Year: 1990).*
Definition of "Wound" from the Oxford English Dictionary online, retrieved Sep. 3, 2020. (Year: 2020).*
Turinsky J, Shangraw RE. Augmented glucose uptake and amino acid release by muscle underlying the burn wound and their moderation by ketone bodies. Exp Mol Pathol. Dec. 1981;35(3):338-46. PMID: 7308412. (Year: 1981).*
Kuppan, Purushothaman et al. Development of Poly(3-hydroxybutyrate-co-3-hydroxyvalerate) Fibers for Skin Tissue Engineering: Effects of Topography, Mechanical, and Chemical Stimuli. BioMacromolecules. 2011, 12: 3156-3165.
Murphy, Kevin D. et al. The Effects of Gammahydroxybutyrate on Hypermetabolism and Wound Healing in a Rat Model of Large Thermal Injury. The Journal of Trauma, Injury, Infection and Critical Care. Nov. 2007: 63(5): 1099-1107.
Magalhaes, Maria Sonia Feicio et al. Effect of a combination of medium chain triglycerides, linoleic acid, soy lecithin and vitamins A and E on wound healing in rats. Acta Cirurgica Brasileira. 2008: 23(3): 262-269.
Kashiwaya, et al., Control of glucose utilization in working perfused rat heart. J Biol Chem. Oct. 14, 1994;269(41): 25502-14.
Demling, MD, Robert H. Nutrition, Anabolism, and the Wound Healing Process: An Overview. ePlasty Open Access Journal of Plastic Surgery. Feb. 3, 2009: 9: 65-94.
Zhao, Zhong et al. A ketogenic diet as a potential novel therapeutic intervention in amyotrophic lateral sclerosis. BMC Neuroscience. Apr. 3, 2006: 7:29.
Seyfried, Thomas N. et al. Cancer as a metabolic disease. Nutrition & Metabolism. 2010: 7:7. http://www.nutritionandmetabolism.com/content/7/1/7.
Tate, Ramon L. et al. Metabolic Fate of 1,3-Butanediol in the Rat: Conversion to b-Hydroxybutyrate. J. Nutrition, 1971: 101: 1719-1726.
Kuroki, Shinsuke et al. Epithelialization in Oral Mucous Wound Healing in Terms of Energy Metabolism. Kobe J. Med. Sci., 2009: 55(2): E5-E15.
Diegelmann, Robert F. et al. Wound Healing: An Overview of Acute, Fibrotic and Delayed Healing. Frontiers in Bioscience. Jan. 1, 2004: 9: 283-289.
Linde, et al., Global cerebral blood flow and metabolism during acute hyperketonemia in the awake and anesthetized rat. J Cereb Blood Flow Metab. Feb. 2006;26(2):170-80.

(Continued)

*Primary Examiner* — Theodore R. West
(74) *Attorney, Agent, or Firm* — Meunier Carlin & Curfman LLC

(57) ABSTRACT

Ketone supplementation, such as through use of precursors of beta-hydroxybutyrate (BHB) and acetoacetate (AcAc), increased blood levels of ketone bodies, increases blood flow and wound closure in ischemic young and aged fisher rats significantly earlier compared to standard diet in aged rats. In vitro experiments with ketone bodies demonstrate decreased mitochondrial and cytosolic ROS in young and aged primary human dermal fibroblasts (PHDF). Ketone bodies increased migration in young and aged PHDFs.

20 Claims, 11 Drawing Sheets

(56) References Cited

OTHER PUBLICATIONS

Maalouf, M., et al., Ketones inhibit mitochondrial production of reactive oxygen species production following glutamate excitotoxicity by increasing NADH oxidation. Neuroscience, 2007. 145(1): p. 256-64.

Maalouf, et al., The neuroprotective properties of calorie restriction, the ketogenic diet, and ketone bodies. Brain Res Rev. Mar. 2009;59(2):293-315.

Milder, & Patel, Modulation of oxidative stress and mitochondrial function by the ketogenic diet. Epilepsy Res. 100(3): p. 295-303.

Ruskin, et al., Reduced pain and inflammation in juvenile and adult rats fed a ketogenic diet. PLoS One. Dec. 23, 2009;4(12):e8349.

Sullivan, et al., The ketogenic diet increases mitochondrial uncoupling protein levels and activity. Annals of neurology, 2004. 55(4): p. 576-580.

Veech, et al., Ketone bodies, potential therapeutic uses. IUBMB Life. Apr. 2001;51(4):241-24.

Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. Mar. 2004;70(3):309-319.

D'Alecy, et al., Substrate-specific stimulation by glucagon of isolated murine brain mitochondrial oxidative phosphorylation. Stroke. Mar.-Apr. 1986;17(2):305-12.

Eiger, et al., Hypoxic tolerance enhanced by beta-hydroxybutyrate-glucagon in the mouse. Stroke. Sep.-Oct. 1980;11(5):513-7.

Alessandro, et al., Effects of Twenty Days of the Ketogenic Diet on Metabolic and Respiratory Parameters in Healthy Subjects. Lung. Dec. 2015;193(6):939-45.

Kirsch, et al., Butanediol induced ketosis increases tolerance to hypoxia in the mouse. Stroke. Sep.-Oct. 1980;11(5):506-13.

Tai, et l., Ketogenic diet prevents cardiac arrest-induced cerebral ischemic neurodegeneration. J Neural Transm (Vienna). Jul. 2008;115(7):1011-7.

Fukao, et al., Enzymes of ketone body utilization in human tissues: protein and messenger RNA levels of succinyl-coenzyme A (CoA):3-ketoacid CoA transferase and mitochondrial and cytosolic acetoacetyl-CoA thiolases. Pediatr Res. Oct. 1997;42(4):498-502.

Grabacka, et al., Regulation of ketone body metabolism and the role of PPAR-alpha. Int'l J Mol Sci. Dec. 13, 2016;17(12):E2093.

Zhang, et al., Mitochondrial acetoacetyl-CoA thiolase (T2) deficiency: T2-deficient patient with "mild" mutation(s) were previously misinterpreted as normal by the coupled assay with tiglyl-CoA. Pediatr Res. Jul. 2004;56(1):60-4.

Kraus et al., The Synthesis and Natural Distribution of the Major Ketone Constituents in Echinacea pallida, Molecules, 2007; 12(3): 406-414.

\* cited by examiner

METABOLIC THERAPY FOR WOUND HEALING

CROSS-REFERENCE TO RELATED APPLICATIONS

This nonprovisional application claims priority to U.S. Provisional Patent Application 61/909,811, entitled "Metabolic Therapy for Wound Healing", filed on Nov. 27, 2013, and claims priority to the application, the contents of which are hereby incorporated by reference.

FIELD OF INVENTION

This invention relates to a therapy for wound healing. More specifically, the invention provides a metabolic treatment to promote wound healing.

BACKGROUND OF THE INVENTION

Upon insult to tissues, such as the skin or other organs, the tissue undergoes an elaborate series of steps to repair the injury. Though the same steps, in the same order, occur in every healing process regardless of the tissue type or nature of injury, the exact mechanisms underlying wound healing are not completely understood. Wound healing is a dynamic continuous process characterized by three main overlapping phases: coagulation, inflammation, a migratory and proliferative process, and a remodeling process. After coagulation, i.e. blood clotting, and inflammation stages, epidermal keratinocytes proliferate and migrate to the wound penumbra, thereby attracting fibroblasts which deposit new collagen and extracellular matrix (Diegelmann & Evans, Wound healing: an overview of acute, fibrotic and delayed healing. Front Biosci. 2004 Jan. 1; 9:283-9). Wound repair is oxygen- and energy-demanding. Increases in blood supply, due to low pH, reduced oxygen tension in the wound site, and excreted factors, satisfy oxygen demands. Increased energy requirements are satisfied by glucose and fatty acids, including palmitic acid, to meet the energy demands of repair (Kuroki, et al., Epithelialization in oral mucous wound healing in terms of energy metabolism. Kobe J Med Sci. 2009 Jun. 5; 55(2):E5-E15).

Wound healing is affected by several factors. These include but are not limited to four key features, as shown in FIG. 1. As wound remodeling occurs after inflammation has been controlled, increases in reactive oxygen species (ROS). In the early stages of normal wound healing, ROS are created by respiratory bursts intended to kill harmful bacteria, thus preventing infection. However, the ROS molecules are highly reactive due to unpaired electrons, and seek to steal and bond with electrons from other molecules. In young healthy cells, the formation of ROS is mitigated by downstream antioxidants such as superoxide dismutases, glutathione peroxidase, and catalase. However, it has been shown that the aged phenotype has decreased levels of antioxidants to scavenge the increased ROS. Increased ROS levels can lead to mitochondrial dysfunction, DNA damage, lipid peroxidation, and even cell death (Schreml, S., et al., Oxygen in acute and chronic wound healing. The British journal of dermatology. 163(2): p. 257-268; Murphy, M. P., How mitochondria produce reactive oxygen species. Biochem J, 2009. 417(1): p. 1-13).

The second factor affecting wound repair is decreased metabolism/ATP production, seen during aging (Pittman, J., Effect of aging on wound healing: current concepts. J Wound Ostomy Continence Nurs, 2007. 34(4): p. 412-5; quiz 416-7). As noted above, wound repair is very energy demanding. Metabolically, wound healing requires the environment to be an anabolic state, having enough macronutrients (carbohydrates, fats, proteins) such as glucose to maintain adequate energy supplies (Demling, R., Nutrition, anabolism, and the wound healing process: an overview. Eplasty, 2009; Stechmiller, J. K., Understanding the role of nutrition and wound healing. Nutr Clin Pract. 25(1): p. 61-8). When adequate levels of these macronutrients are limited, the wound is an effective parasite on the substrates available in the rest of the body. The metabolic response to injury is characterized as having "ebb" phase or hypometabolic phase during the first few hours or days of injury followed by a "flow" phase or hypermetabolic phase in the weeks to months that follow the injury (Molnar, J. A., Nutrition and wound healing. CRC, 2007).

The third factor affecting wound repair is blood flow, which affects the amount of oxygen available for metabolic processes associated with wound repair. Normal blood flow is required for nutrients and oxygen to reach the wound site to preserve a characteristic tissue pO2 (~30-40 mmHg). When the blood flow is impaired, the wound is characterized as ischemic and the wound bed doesn't receive the nutrients it needs to heal. In the wound area, decreased blood to the cells results in up to a 90% reduction in ATP compared to normal aerobic energy production (Demling, Nutrition, anabolism, and the wound healing process: an overview. Eplasty. 2009 Feb. 3; 9:e9).

Chronic wounds resulting from impaired wound healing represents an immense economic and social epidemic in the United States. Chronic wounds are those that have failed to heal due to impaired wound healing resulting from inflammation, restricted nutrient and oxygen and impaired tissue metabolism. Such wounds result in increased morbidity and mortality of patients. This leads to an estimated $25 billion annual cost in treating chronic wounds, which is rapidly growing due to increased health care costs, an aging population, an increase in diabetes and obesity, and the expanding need for wound care. The amount of money spent on wound care, the loss of productivity for afflicted individuals and the families that care for them, and their diminished quality of life come at great cost to our society (Sen, C., et al., Human skin wounds: a major and snowballing threat to public health and the economy. Wound repair and regeneration: official publication of the Wound Healing Society [and] the European Tissue Repair Society, 2009. 17(6): p. 763-771). For example, about 60% of spinal cord injury patients experience chronic ulceration costing $14,000 to $25,000 per patient per year (Diegelmann & Evans, Wound healing: an overview of acute, fibrotic and delayed healing. Front Biosci. 2004 Jan. 1; 9:283-9).

Aging and poor metabolic health are associated with impaired wound healing and reduced tissue perfusion, impaired nutrient and oxygen delivery, decreased adenosine triphosphate (ATP) production and inflammation in the wound tissue. In the United States, it is estimated that there are 1.8 million new cases of chronic wounds annually, with the majority occurring in the elderly. Reactive oxygen species (ROS) damage is augmented in aged patients leading to redox imbalance and is a key characteristic in impaired wound healing. However, there are presently no therapeutic options available to enhance wound healing, but rather prevent unwanted microbial growth. As the number of aged individuals increases in developed countries, such as the U.S., the need for treatments to address chronic wound ulceration is desperately needed.

SUMMARY OF THE INVENTION

Aging and poor metabolic health are associated with impaired wound healing that results from impaired tissue perfusion, impaired nutrient and oxygen delivery, decreased adenosine triphosphate (ATP) production and inflammation in the wound tissue. Ketone bodies, such as beta-hydroxybutyrate (BHB) and acetoacetate (AcAc), can assist in reversing impaired wound healing by decreasing ROS production, increase ATP synthesis, decrease inflammation, and increase blood perfusion.

Ketone bodies are naturally produced in the body as an alternative fuel when glucose and insulin levels are low, e.g., during starvation. The body switches from glucose-fueled ATP production to breaking down fats to generate ATP. Diets that increase ketone levels have been used to manage epilepsy, and are currently being investigated as adjunct treatment for cancer (Seyfried, & Shelton, Cancer as a metabolic disease. Nutr Metab (Lond). 2010; 7:7), amyotrophic lateral sclerosis (Zhao, et al., A ketogenic diet as a potential novel therapeutic intervention in amyotrophic lateral sclerosis. BMC Neurosci. 2006 Apr. 3; 7:29), and traumatic brain injury (Prins, Cerebral metabolic adaptation and ketone metabolism after brain injury. J Cereb Blood Flow Metab. 2008 Jan. 28(1):1-16).

Ketone bodies, such as beta-hydroxybutyrate and acetoacetate, have been shown to decrease ROS production (Milder, & Patel, Modulation of oxidative stress and mitochondrial function by the ketogenic diet. Epilepsy Res. 100(3): p. 295-303; Maalouf, M., et al., Ketones inhibit mitochondrial production of reactive oxygen species production following glutamate excitotoxicity by increasing NADH oxidation. Neuroscience, 2007. 145(1): p. 256-64; Sullivan, et al., The ketogenic diet increases mitochondrial uncoupling protein levels and activity. Annals of neurology, 2004. 55(4): p. 576-580) increase ATP synthesis (Veech, et al., Ketone bodies, potential therapeutic uses. IUBMB Life. 2001 April; 51(4):241-247; Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. 2004 March; 70(3):309-319; Maalouf, et al., The neuroprotective properties of calorie restriction, the ketogenic diet, and ketone bodies. Brain Res Rev. 2009 March; 59(2):293-315) make ATP production more efficient (Veech, et al., Ketone bodies, potential therapeutic uses. IUBMB Life. 2001 April; 51(4):241-247; Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. 2004 March; 70(3):309-319; Maalouf, et al., The neuroprotective properties of calorie restriction, the ketogenic diet, and ketone bodies. Brain Res Rev. 2009 March; 59(2):293-315), decrease inflammation (Ruskin, et al., Reduced pain and inflammation in juvenile and adult rats fed a ketogenic diet. PLoS One. 2009 Dec. 23; 4(12):e8349), and increase blood perfusion (Linde, et al., Global cerebral blood flow and metabolism during acute hyperketonemia in the awake and anesthetized rat. J Cereb Blood Flow Metab. 2006 February; 26(2):170-80; Kashiwaya, et al., Control of glucose utilization in working perfused rat heart. J Biol Chem. 1994 Oct. 14; 269(41):25502-14).

As wound healing is affected by increases in reactive oxygen species (ROS) during the inflammation stage of repair, decreased metabolism/ATP production, and decreased blood flow, ketone bodies, such as beta-hydroxybutyrate (BHB) and acetoacetate (AcAc), were used to reverse impaired wound healing by supplying an alternative fuel, reducing ROS production and increase levels of adenosine, a potent vasodilator. Ketones are an energy substrate that reduce ROS production in the brain and heart, and thus may augment wound healing. Using a ketogenic supplement to increase levels of ketone bodies in the systemic physiology of the body was hypothesized to shift the metabolic state of a chronic wound environment, and thus mitigate some of the negative effects of aging on wound healing and promote wound healing processes.

Accordingly, a method of improving wound healing by administering at least one ketone to a patient having a wound is provided. The ketone is optionally R,S-1,3-Butanediol, beta-hydroxybutyrate precursor, acetoacetate, acetoacetate precursor, or at least one medium chain triglycerides and beta-hydroxybutyrate mineral salt.

Ketone precursors include, without limiting the scope of the invention combinations of at least one medium chain fatty acid, or an ester thereof such as a medium chain triglyceride, and a β-hydroxybutyrate ketone source or precursor. There are numerous sources of ketones and ketogenic precursors. Nonlimiting examples of the beta-hydroxybutyrate compound include beta-hydroxybutyrate salts such as sodium beta-hydroxybutyrate and arginine beta-hydroxybutyrate, potassium beta-hydroxybutyrate, calcium beta-hydroxybutyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, beta-hydroxy butyrate sodium salt, beta-hydroxy butyrate potassium salt, beta-hydroxy butyrate calcium salt, beta-hydroxy butyrate magnesium salt, or a combination of salts. Nonlimiting examples of combinations of beta-hydroxybutyrate salts include sodium beta-hydroxybutyrate and arginine beta-hydroxybutyrate, or beta-hydroxy butyrate sodium salt and beta-hydroxy butyrate potassium salt. Other β-hydroxybutyrate ketone sources include, without limiting the scope, 1,3-butanediol, ethyl acetoacetate, and ethyl beta-hydroxybutyrate. The compounds, are optionally administered between 2 grams and 50 grams, between 5 grams and 30 grams, or between 10 grams and 20 grams. For example, the ketone compounds are optionally administered at 2 grams, 4 grams, 5 grams, 6 grams, 7 grams, 8 grams, 9 grams, 10 grams, 11 grams, 12 grams, 13 grams, 14 grams, 15 grams, 17 grams, 19 grams, 20 grams, 22 grams, 24 grams, 26 grams, 28 grams, 30 grams, 32 grams, 34 grams, 36 grams, 38 grams, 40 grams, 42 grams, 44 grams, 46 grams, 48 grams, or 50 grams.

In some variations of the invention, the beta-hydroxy butyrate compound is histidine beta-hydroxybutyrate, ornithine beta-hydroxybutyrate, creatine beta-hydroxybutyrate, agmatine beta-hydroxybutyrate, or citrulline beta-hydroxybutyrate. The compound is optionally a racemic DL-beta hydroxybutyrate or the single isomer R-beta hydroxybutyrate.

Non-limiting examples and sources of the medium chain fatty acid, or an ester thereof such as a medium chain triglyceride, include coconut oil, coconut milk powder, fractionated coconut oil, palm oil, palm kernel oil, caprilic acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc. Oils may be spray dried onto solid supports such as maltodextrin to facilitate delivery in powder form. The at least one medium chain triglyceride is optionally administered at between 5 grams and 50 grams, between 10 grams and 40 grams, or between 15 grams and 30 grams. As a nonlimiting example, the medium chain triglyceride is administered at 5 grams, 6 grams, 7 grams, 8 grams, 9 grams, 10 grams, 11 grams, 12 grams, 13 grams, 14 grams, 15 grams, 17 grams, 19 grams, 20 grams, 22 grams, 24 grams, 26 grams, 28 grams, 30 grams, 32 grams, 34 grams, 36 grams, 38 grams 40 grams.

Beta-Hydroxybutyrate (BHB; 5 mM) reduces cytosolic and mitochondrial ROS production in both young and aged primary human dermal fibroblasts. Primary human dermal fibroblasts (HDFs, passaged 2-8) from young and aged donors (24 to 88 years) were incubated in the absence or presence of BHB for 72 hours prior to stress with 100 µM tert-buytl-hydrogen peroxide for 3 hours. ROS production was measured fluorescently with dihydroethidium (DHE, cytosolic) and MitoSOX Red (mitochondrial) in triplicate, N=6. In the cytosol, aged HDFs produced 28% ($p=<0.001$)) more ROS basally compared to their young counterparts. When incubated in BHB for 72 hours, ROS production in the young HDFs decreased by 40% ($p=<0.0001$) and by 41% ($p=<0.0001$) in the aged. In the mitochondria, aged HDFs produced 27% ($p=<0.0001$) more ROS at baseline than the young HDFs, consistent with observations in cytosol. When incubated in BHB, ROS production was reduced in the young by 29% ($p<0.0001$) and in the aged by 51% ($p<0.0001$); the aged ROS production was no longer significantly different from the young. Ketone supplementation did not significantly change proliferation in the HDFs, but did increase migration in both young and aged HDFs. As such, ketone supplementation is useful against redox stress and augments wound healing, shifting redox homeostasis in HDFs, especially in the elderly.

The compositions have been found especially useful when used to produce clinical ketosis in the patient. Preferably, blood levels above 0.5 mmol/L (mild clinical ketosis) through less than 10 mmol/L are used. In specific embodiments, the target blood levels are between about 1.0 mmol/L and about 3.0 mmol/L. Administration of the compositions at about 1 g/kg/day achieves mild ketosis, whereas 10 g/kg/day achieves high levels of ketosis. As such the ketone compositions are optionally administered at about 1 g/kg/day to about 10 g/kg/day. Nonlimiting examples include 1 g/kg/day, 1.5 g/kg/day, 2 g/kg/day, 2.5 g/kg/day, 3 g/kg/day, 3.5 g/kg/day, 4 g/kg/day, 4.5 g/kg/day, 5 g/kg/day, 5.5 g/kg/day, 6 g/kg/day, 7 g/kg/day, 8 g/kg/day, 8.5 g/kg/day, 9 g/kg/day, 9.5 g/kg/day, and 10 g/kg/day.

The compositions can also be used to reducing or treating redox stress in wound repair by administering at least one ketone to a patient having a wound. The compositions provided above are useful for the methodology of reducing or treating redox stress in wound repair. In specific variations, the compositions are used to produce clinical ketosis in the patient, such as blood levels above 0.5 mmol/L through less than 10 mmol/L. In specific embodiments, the target blood levels are between about 1.0 mmol/L and about 3.0 mmol/L.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
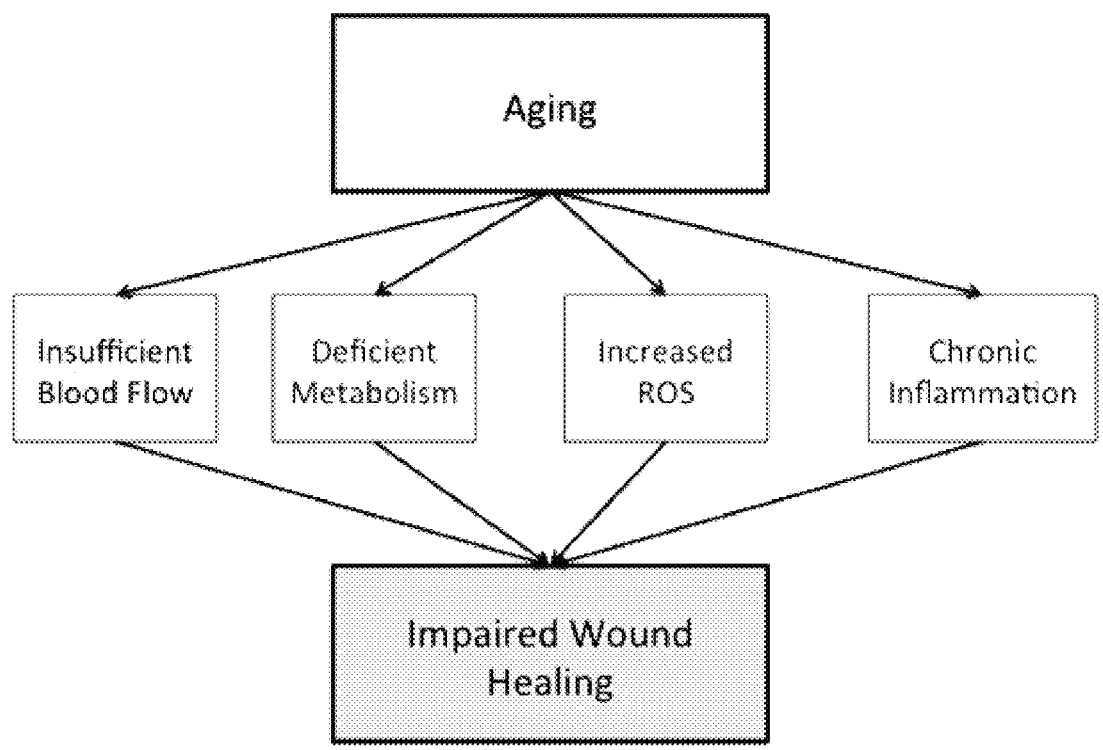
FIG. 1 is a diagram of wound healing factors.

As used herein, the singular forms "a," "an" and "the" include plural referents unless the context clearly dictates otherwise. Thus, for example, reference to "a ketone precursor" includes a mixture of two or more ketone precursors and the like, unless otherwise specified.

As used herein, "about" means approximately or nearly and in the context of a numerical value or range set forth means±15% of the numerical. "About" is understood to refer to numbers in a range of numerals. Moreover, all numerical ranges herein should be understood to include all integer, whole or fractions, within the range.

As used herein "beta-hydroxybutyrate," also known as BHB or BHB, is a carboxylic acid having the general formula $CH_3CH_2OHCH_2COOH$ which may be utilized by a patient's body as a fuel source during instances of low glucose levels in the patient and is considered a ketone body. In the present invention, salt variants of beta-hydroxybutyrate are disclosed.

"Ketosis" as used herein refers to a subject having blood ketone levels >0.5 mmol/L. Ketone levels sustained above 0.5 mmol/L and ideally in the range of 1.0 to 3.0 mmol/L appear to offer the most therapeutic effects in humans. Levels of ketosis above 10.0 mmol/L are associated with signs of ketoacidosis. Ketosis may improve mitochondrial function, elevate Krebs cycle intermediates (e.g. succinate, fumarate), decrease ROS production, reduce inflammation, elevated adenosine and increase the activity of neurotrophic factors associated with enhanced wound repair.

"Keto-adaptation" as used herein refers to prolonged nutritional ketosis (>1 week) to achieve a sustained non-pathological "mild ketosis" or "therapeutic ketosis."

The term "medium chain triglycerides" (MCT) are molecules having a glycerol backbone attached to three medium chain fatty acids. Medium chain fatty acids range from 6 to 12 carbon atoms in length. Exemplary fatty acids are caprylic acid, also known as octanoic acid, comprising 8 carbon molecules, and capric acid, also known as decanoic acid, comprising 10 carbon molecules.

As used herein "patient", means members of the animal kingdom, including mammals, such as but not limited to, primates including humans, gorillas and monkeys; rodents, such as mice, fish, reptiles and birds. As used herein "animal" means a multicellular, eukaryotic organism classified in the kingdom Animalia or Metazoa. The term includes, but is not limited to, mammals. Non-limiting examples include, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals. The patient may be any animal requiring therapy, treatment, or prophylaxis, or any animal suspected of requiring therapy, treatment, or prophylaxis. The term treatment, as used in this definition only, is intended to mean that regiment described is continued until the underlying tissue damage is resolved, whereas therapy requires that the regiment alleviate one or more symptoms of the underlying damage, such as formation of reactive oxygen species.

As used herein, the term "therapeutically effective amount" refers to that amount of a therapy (e.g., a ketogenic agent) sufficient to result in the amelioration of oxidation via reactive oxygen species or improving the outcome of wound healing, prevent chronic ulceration, reduce scar formation, or to enhance or improve the therapeutic effect(s) of another wound repair therapy.

As used herein, "treating" means improving wound healing or lessening the effects of redox damage to a cell. In specific embodiments, treating means preventing or alleviating (reducing or eliminating) the symptoms of redox damage in the wound or wounds of a patient when administered one or more times over a suitable time period.

The term "pharmaceutically acceptable salt" means a salt that possesses the desired pharmacological activity of the parent compound. Such salts include, without limiting the scope of the invention, salt derivatives prepared by methods known to those of skill in the art. For example, acid addition salts, formed with inorganic acids, such as hydrochloric acid, hydrobromic acid, sulfuric acid, nitric acid, phosphoric acid, Lewis acids, or formed with organic acids, such as acetic acid, propionic acid, hexanoic acid, cyclopentancepropionic acid, glycolica acid, pyruvic acid, lactic acid, malonic acid, succinic acid, malic acid, maleic acid, fumaric acid, and citric acid. Alternatively, the salt derivatives are formed when an acidic proton present in the patent compound is replaced by a metal ion, such as an alkali metal, an alkaline earth ion, or coordinates with an organic base. Some non-limiting exemplary inorganic bases include aluminum hydroxide, calcium hydroxide, potassium hydroxide, sodium carbonate, and sodium hydroxide.

The term "administration" or "administering" is used to describe the process in which individual ketone esters or beta-hydroxybutyrate salts in any combination with medium chain fatty acid derivatives are delivered to a subject. The composition may be administered in various ways including oral, intragastric, and parenteral (referring to intravenous and intra-arterial and other appropriate parenteral routes), among others. Each of these conditions may be readily treated using other administration routes of beta-hydroxybutyrate salts in combination with medium chain triglycerides, derivatives, or any combination thereof to treat a disease or condition.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., weight loss or treatment of cancer or neurological disease, and the like. The duration of administration of the agent, e.g., the period of time over which the agent is administered, can vary, depending on any of a variety of factors, including patient response, desired effect of treatment, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

The amount of the beta-hydroxybutyrate salts in combination with medium chain triglycerides or derivatives will depend on absorption, distribution, metabolism, and excretion rates of the beta-hydroxybutyrate salts in combination with medium chain triglycerides or derivatives, the particular beta-hydroxybutyrate salts in combination with medium chain triglycerides or derivatives, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

Statistics

All data are presented as the mean±standard error of the mean (SEM). All calculations were performed using statistical analysis software GraphPad PRISM™ version 6.0a. Statistical significance was defined as $p<0.05$. All data were compared to control at the applicable time points using a two-way ANOVA with Dunnet's multiple comparisons test.

Example 1

Figure 2A:
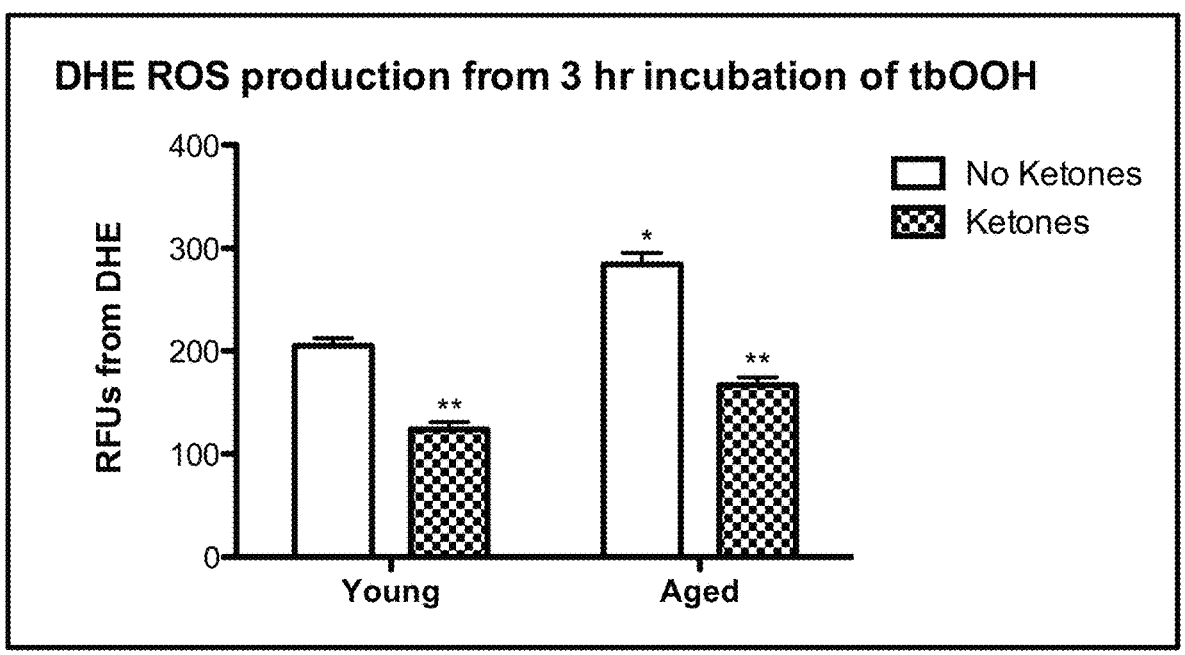
FIGS. 2(A) and (B) are graphs showing ketone Supplementation Decreases Mitochondrial and Cytosolic ROS production in Primary Human Dermal Fibroblasts (PHDFs)
Figure 2B:
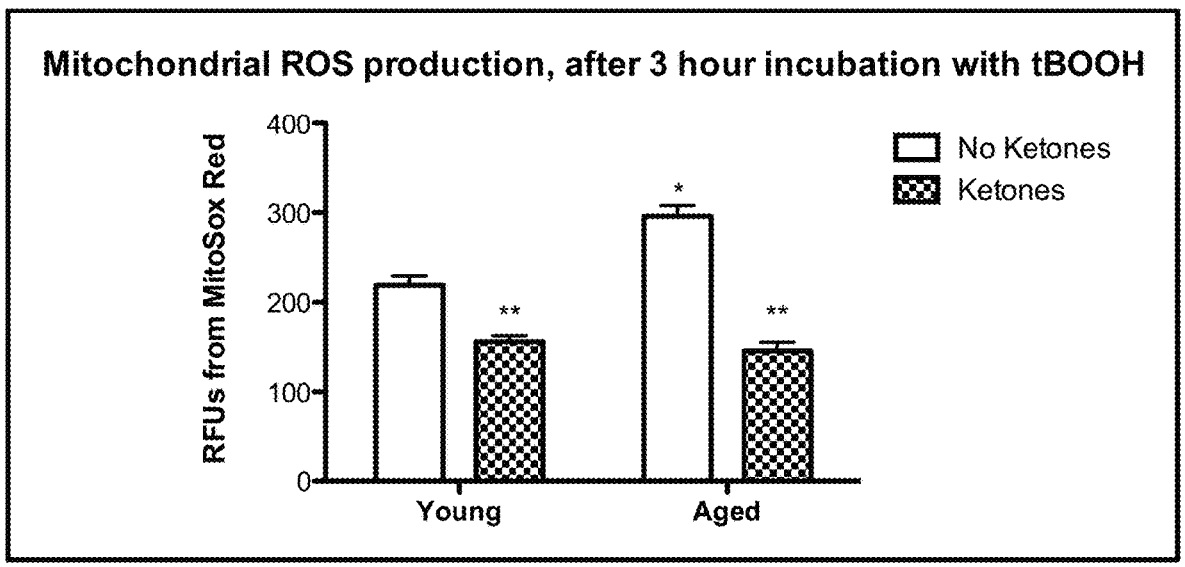

Primary human dermal fibroblasts (HDFs, passaged 2-8) from young and aged donors (24 to 88 years) were incubated in the absence or presence of 5 mM beta-hydroxybutyrate (BHB) for 72 hours. To simulate a wound environment, the cells were then stressed with 100 µM tert-butyl-hydrogen peroxide for 3 hrs. ROS production was measured fluorescently with dihydroethidium (DHE, cytosolic) and Mitosox Red (mitochondrial) in triplicate, N=6. In the cytosol, seen in FIG. 2(A), aged HDFs produced 25% ($p=0.003$) more ROS basally compared to their young counterparts. This is consistent with the knowledge that aged cells have less antioxidants to mitigate the ROS production in a stressed environment. When incubated in 5 mM BHB for 72 hours, young HDFs ROS production decreased by 40% (p=<0.0001) and aged ROS production decreased by 41% (p=<0.0001). In the mitochondria, as seen in FIG. 2(B), aged HDFs produced 27% (p=<0.0001) more ROS at baseline than the young HDFs, consistent with observations in cytosol. When incubated in BHB, ROS production was reduced in the young by 29% (p<0.0001) and in the aged by 51% (p<0.0001) compared to the controls. The aged ROS production was no longer significantly different from the young HDFs ROS production, there by normalizing ROS production in the aged cells to young levels. Significance calculated using one-way ANOVA and t-tests on Prism 6 software.

Figure 3A:
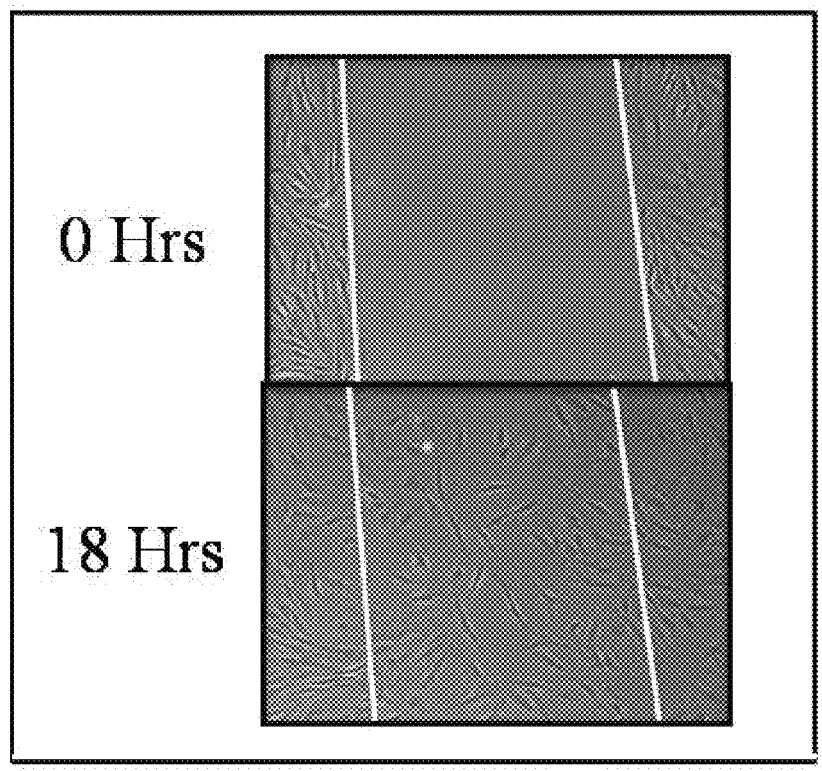
FIGS. 3(A) and (B) show ketone Supplementation Increases Migration in Young and Aged PHDFs. (A) Are images of cell cultures treated with or without BHB and subjected to pipette scratching at 0 hrs and 18 hours. (B) is a graph showing migration patterns of young and old cells in culture 18 hours after the culture was scratched.
Figure 3B:
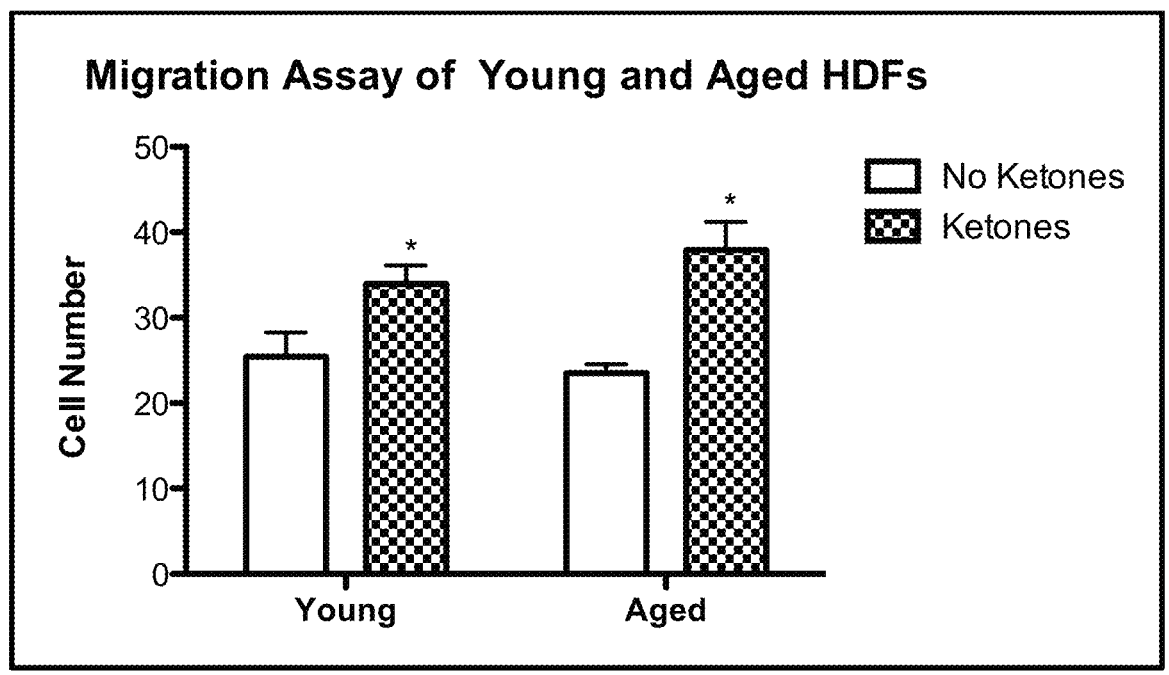

To determine if supplementation of ketones would have functional differences in the cells, a scratch migration assay was conducted, as seen in FIG. 3(A). Young and aged HDFs were grown to confluence in 0.2% FBS 5 mM glucose DMEM media, cells were treated with or without the presence of 5 mM BHB for 72 hours, cells were scratched with 200 uL yellow pipette tip. After 18 hours, migrated cells were counted using Dapi staining. Young and aged cells, treated with ketones, migrated significantly more (p=0.0260 and p=0.0004) compared to the controls without treatment, as seen in FIG. 3(B). These data support that ketone supplementation decreases ROS production an underlying characteristic of chronic wounds and it aids migration of HDFs, showing that ketone supplementation may aid in wound healing.

Example 2

Figure 4:
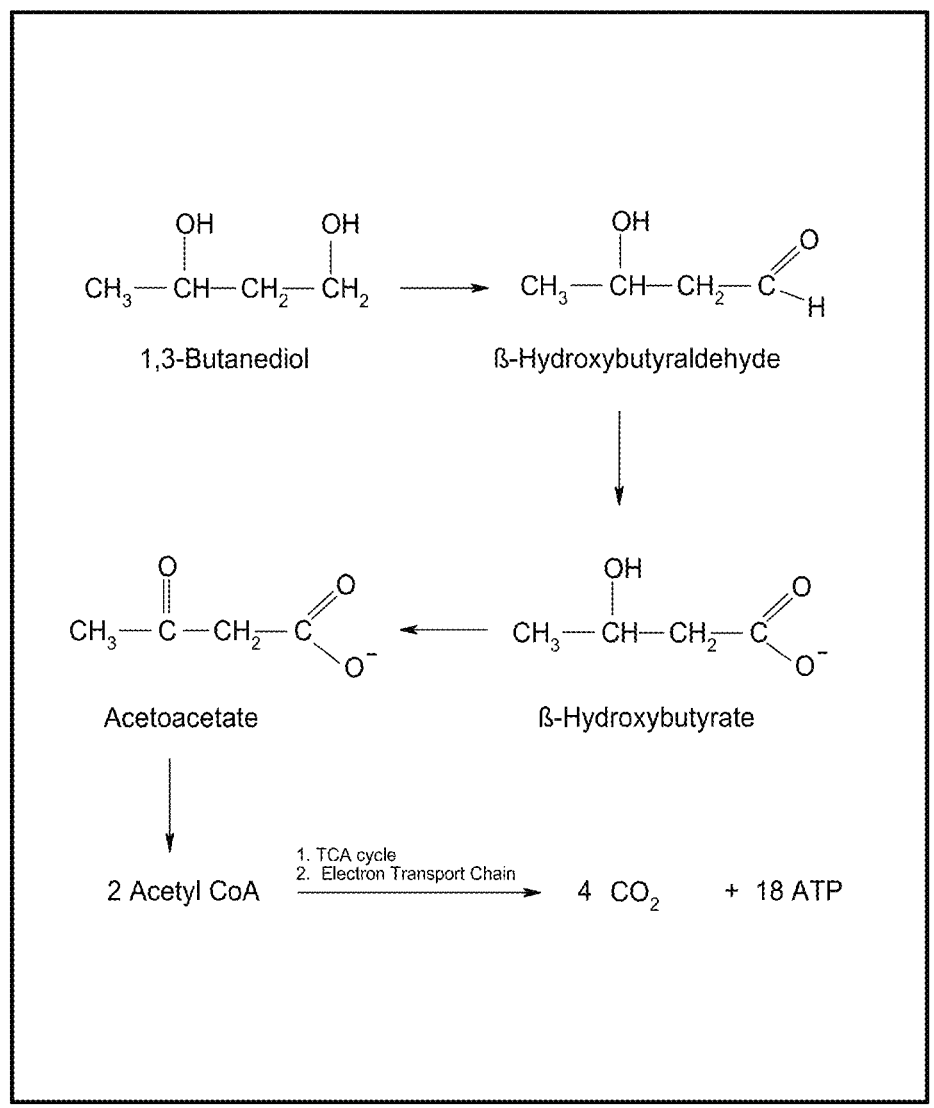
FIG. 4 is an illustration of metabolism of butanediol.

One week prior to surgery all rats were fed ad libitum, the control diet of standard rodent chow (2018 Teklad Global 18% Protein Rodent Diet, Harlan Laboratories) mixed with peanut butter and $H_2O$ to form a pudding to condition the rats away from pelleted food. On the day of ischemic flap creation, young and aged rats were randomly assigned to one of three study groups: Control standard diet (SD), ketone supplement diet #1 (KS1) or ketone supplement diet #2 (KS2). Control rats were fed a combination of standard rodent chow (2018 Teklad Global 18% Protein Rodent Diet, Harlan Laboratories) mixed into a pudding and fed ad libitum. Rats in KS1 group received a diet of standard rodent chow mixed with 20 W/W % 1,3-Butanediol (Sigma-Aldrich, St., St. Louis, Mo.) by weight ad libitum. Tate, et al. investigated the metabolic fate of 1,3-Butanediol in rats concluding that alcohol dehydrogenase catalyzes the initial step of 1,3-Butanediol to β-hydroxybutyraldehyde which is rapidly oxidized to β-hydroxybutyrate (BHB) by aldehyde dehydrogenase. This conversion happens in the liver of the animal, the ketones are then systemically transported where subsequent metabolic steps convert BHB to acetoacetate and acetyl CoA followed by entry of acetyl CoA into the TCA cycle to eventually produce ATP, as seen in FIG. 4 (Tate, et al., Metabolic Fate of 1,3-butanediol in the rat: conversion to beta-hydroxybutyrate. J Nutr. 1971 December; 101(12):1719-26). Rats in the KS2 group received a diet of standard rodent chow, 10 W/W % MCT oil (food grade with a C8:C10 of 55:45) by weight and 10 W/W % βHB mineral salt solution (10% βHB) by weight ad libitum. Diets were continuously replaced to maintain freshness and allow rat to feed ad libitum.

Target blood levels for wound healing were above 0.5 mmol/L (mild clinical ketosis) through less than 10 mmol/L. Administration of the compositions at about 1 g/kg/day achieves mild ketosis, whereas 10 g/kg/day achieves high levels of ketosis. In specific embodiments, the target blood levels are between about 1.0 mmol/L and about 3.0 mmol/L.

Figure 5:
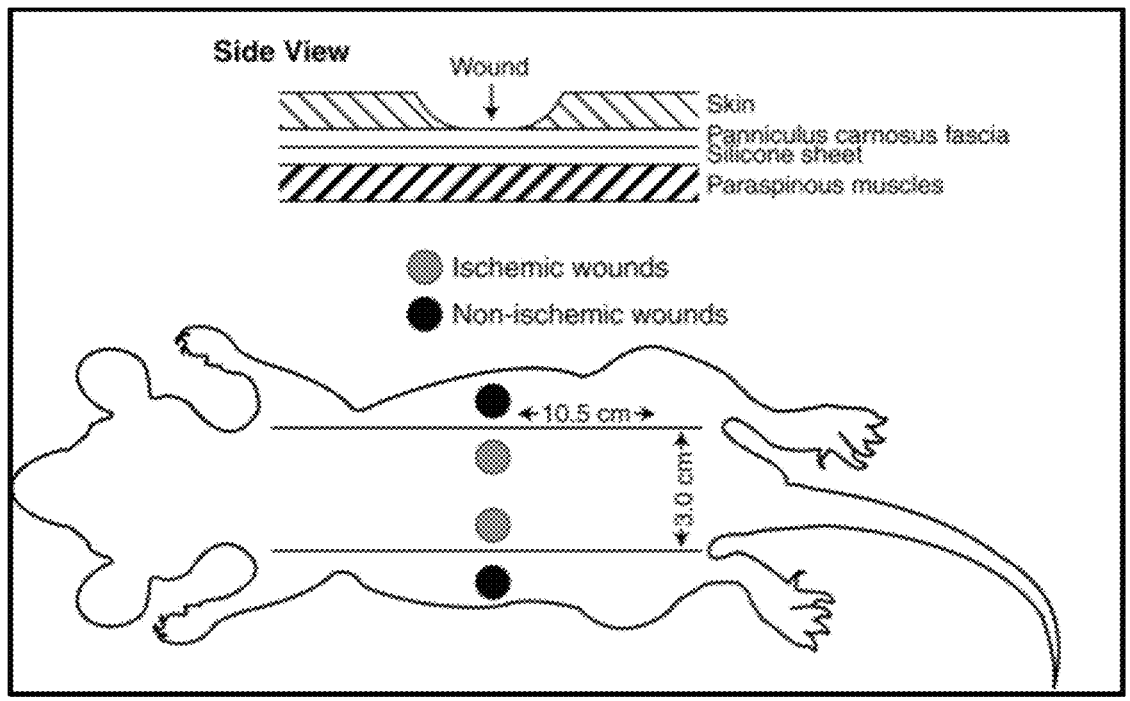
FIG. 5 is an illustration model of wound healing in a rat.

In all Fisher rats, a dorsal bi-pedicle 10.5 cm×3 cm flap, seen in FIG. 5 was surgically created, as described by Gould, et al. (See, Gould, et al., Optimization and validation of an ischemic wound model. Wound Repair Regen. 2005 November-December; 13(6):576-82). Briefly, a silicone sheet was placed under the panniculus carnosus fascia and above the paraspinous muscles, limiting revascularization in that area causing the flap to become ischemic. Two 6 mm punches were created in the flap, extending just above the fascia creating ischemic wounds as well as two 6 mm punches were created laterally where there isn't silicone sheet, giving the control non-ischemic wounds.

Once a week during dressing changes, Laser Doppler was used to measure blood flow in the ischemic flap. Laser Doppler measures the total local microcirculatory blood perfusion including the perfusion in capillaries (nutritive flow), arterioles, venules and shunting vessels. The technique is based on the emission of a beam of laser light carried by a fiber-optic probe. The light is then scattered and partly absorbed by the tissue being studied. Light hitting moving blood cells undergoes a change in wavelength (Doppler shift) while light hitting static objects is unchanged. The magnitude and frequency distribution of these changes in wavelength are directly related to the number and velocity of the blood cells in the sample volume. The information is picked up by a returning fiber, converted into an electronic signal and analyzed.

Figure 6:
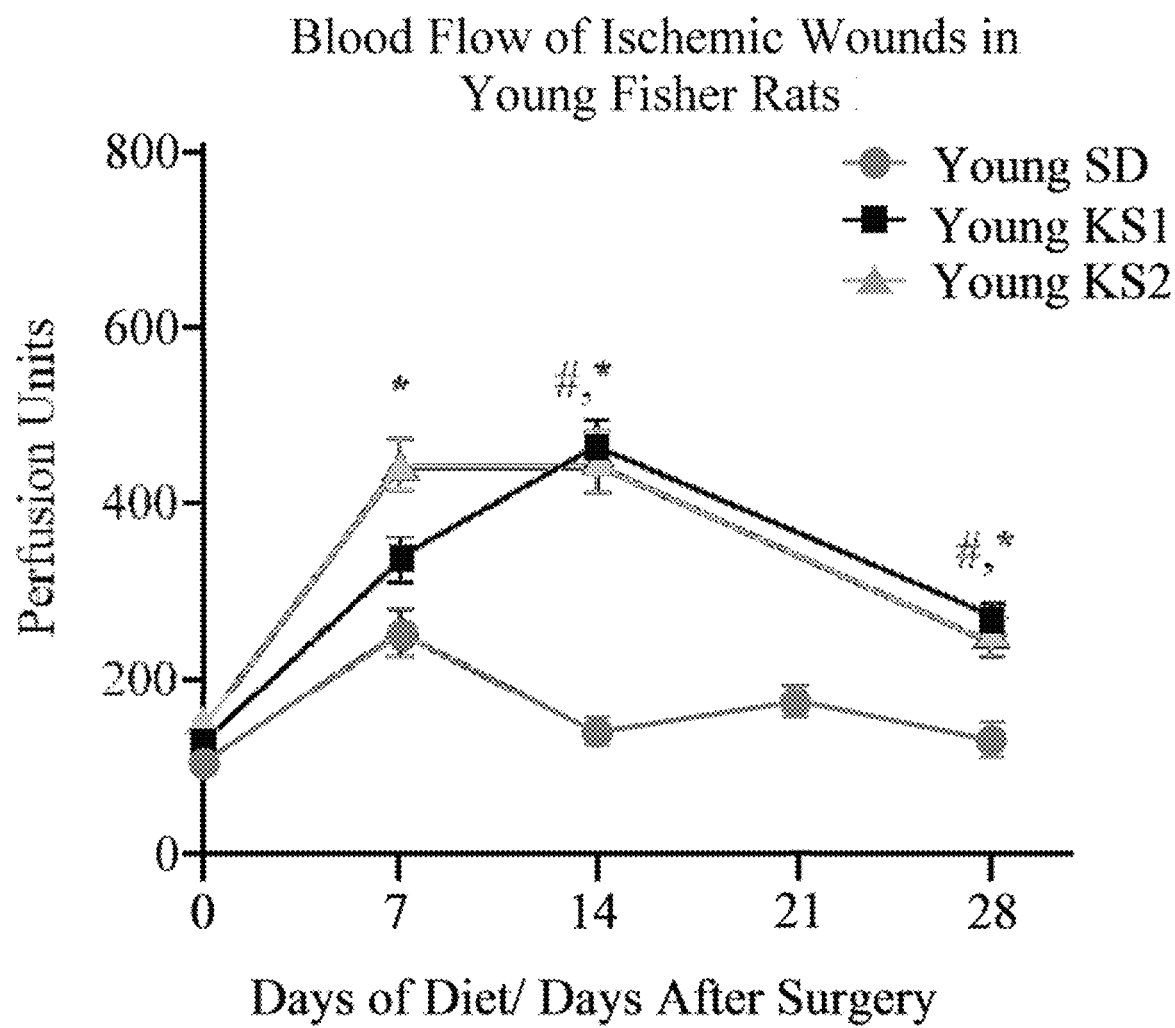
FIG. 6 is a graph showing ketone supplementation increases blood flow in young rats.
Figure 7:
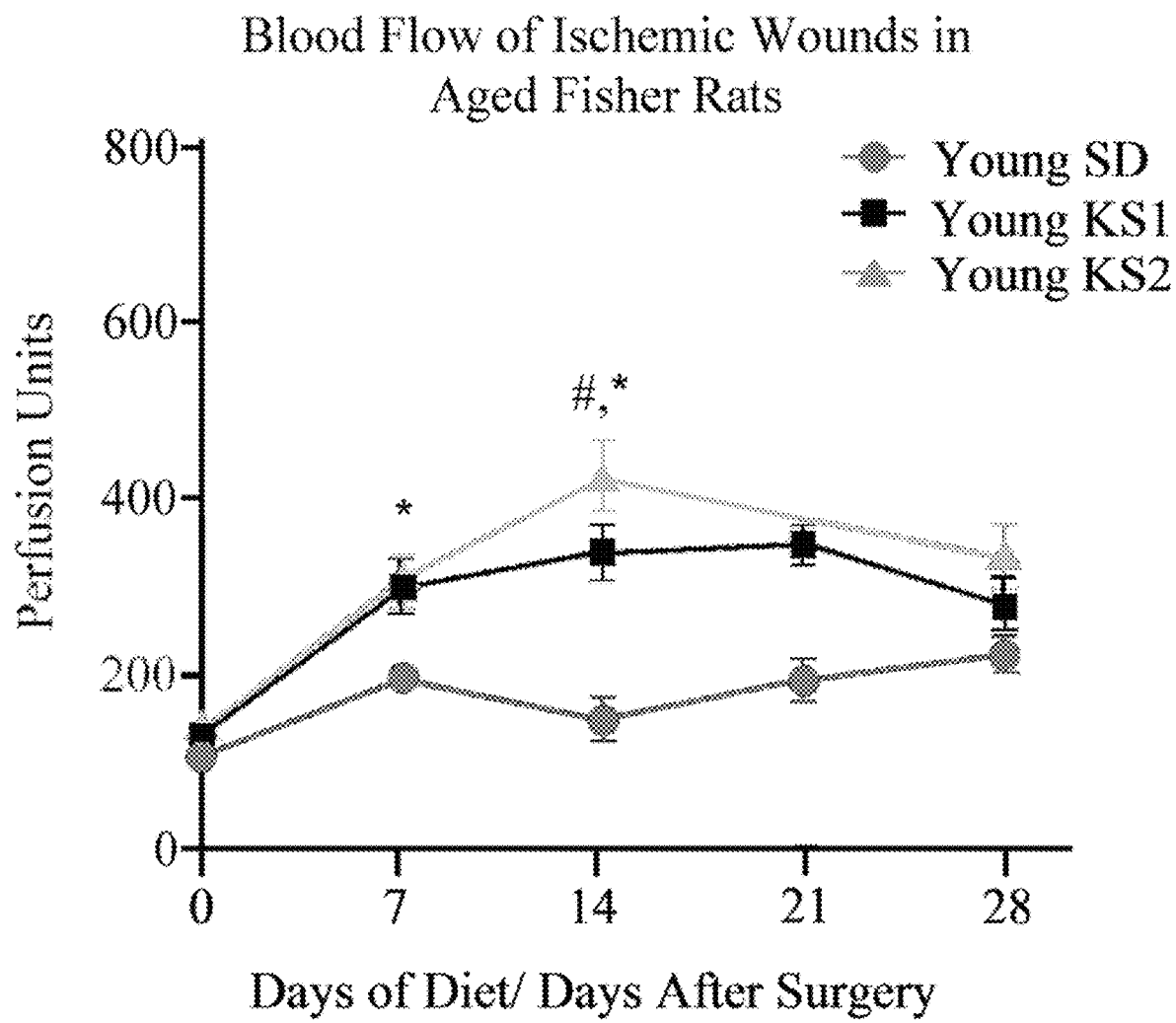
FIG. 7 is a graph showing ketone supplementation increases blood flow in aged rats.

Laser Doppler imaging of the ischemic peri-wound tissue demonstrated significantly increased blood flow in young rats compared to old rats (n=10 per group). By day 7, ketone supplementation in young rats showed a minor improvement in blood flow (p=0.0007 for KS2), as seen in FIG. 6. By day 14, both ketone diets showed significantly enhanced blood flow in the young rats 14 (p<0.0001 for KS1; p=0.0001 for KS2), which continued through day 28 (p<0.0002 for KS1; p=0.0036 for KS2) compared to control, as seen in FIG. 6. Doppler also demonstrated significant increased blood flow in the aged rats. A day 7, ketone supplemented diet showed about a 50% increase in blood flow (p=0.0305 for KS2), as seen in FIG. 7. By day 14, there was a 100% increase in blood flow (p=0.0039 for KS1; p=0.0008 for KS2) compared to control, as seen in FIG. 7.

Figure 8:
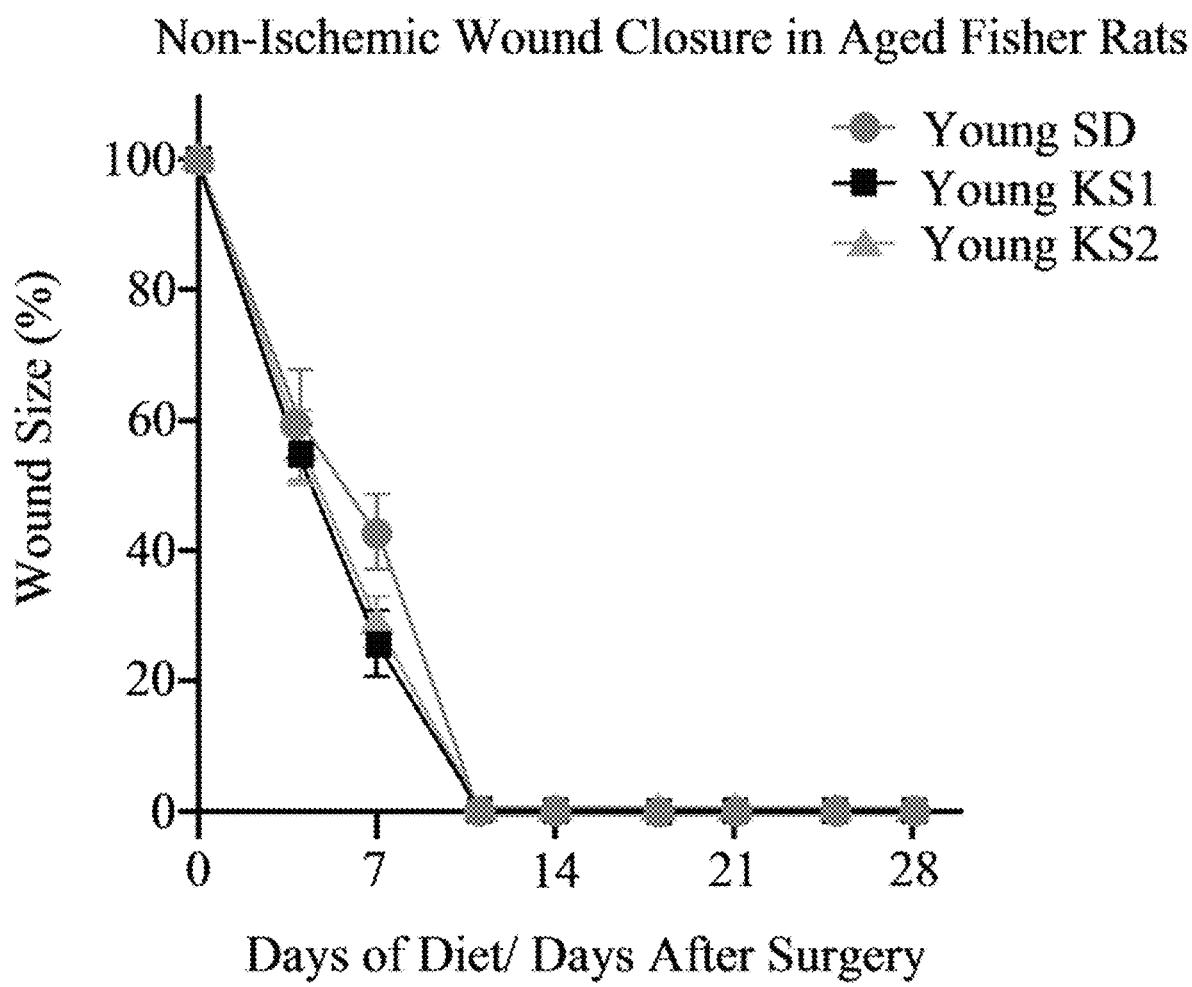
FIG. 8 is a graph showing no change in wound closure time in the control non-ischemic wounds for the young Fisher rats (n=10 per group) by three days.
Figure 9:
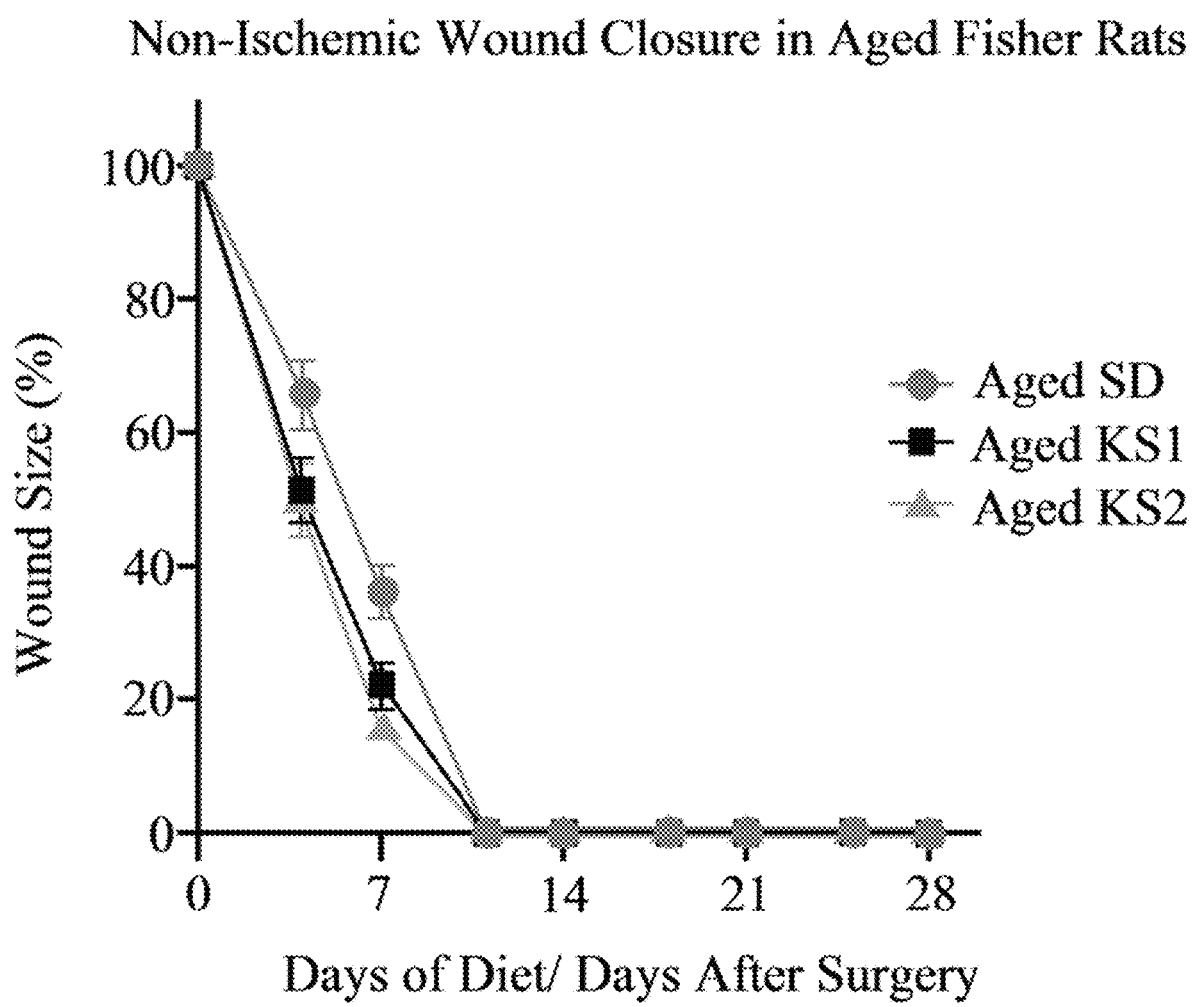
FIG. 9 is a graph showing no significant change in wound closure time in the control non-ischemic wounds for the aged Fisher rats (n=10 per group) by three days.

Wound size was measured pictorially every three days and analyzed using Image J software and compared to Day 0. Significance determined using one-way ANOVA and t-tests on Prism 6 software. While ketone diet treatment increased wound closure slightly at day 7, no significant difference was seen in wound closure time in the control non-ischemic wounds versus ketone supplemented treatment for the young Fisher rats (n=10 per group), as seen in FIG. 8. In aged rats with non-ischemic wounds (n=10 per group), wound closure was similarly increased slightly up through day 7 (p=0.0472 for KS1; p=0.0001 for KS2), but the rate of wound closure was not significant, as seen in FIG. 9.

Figure 10:
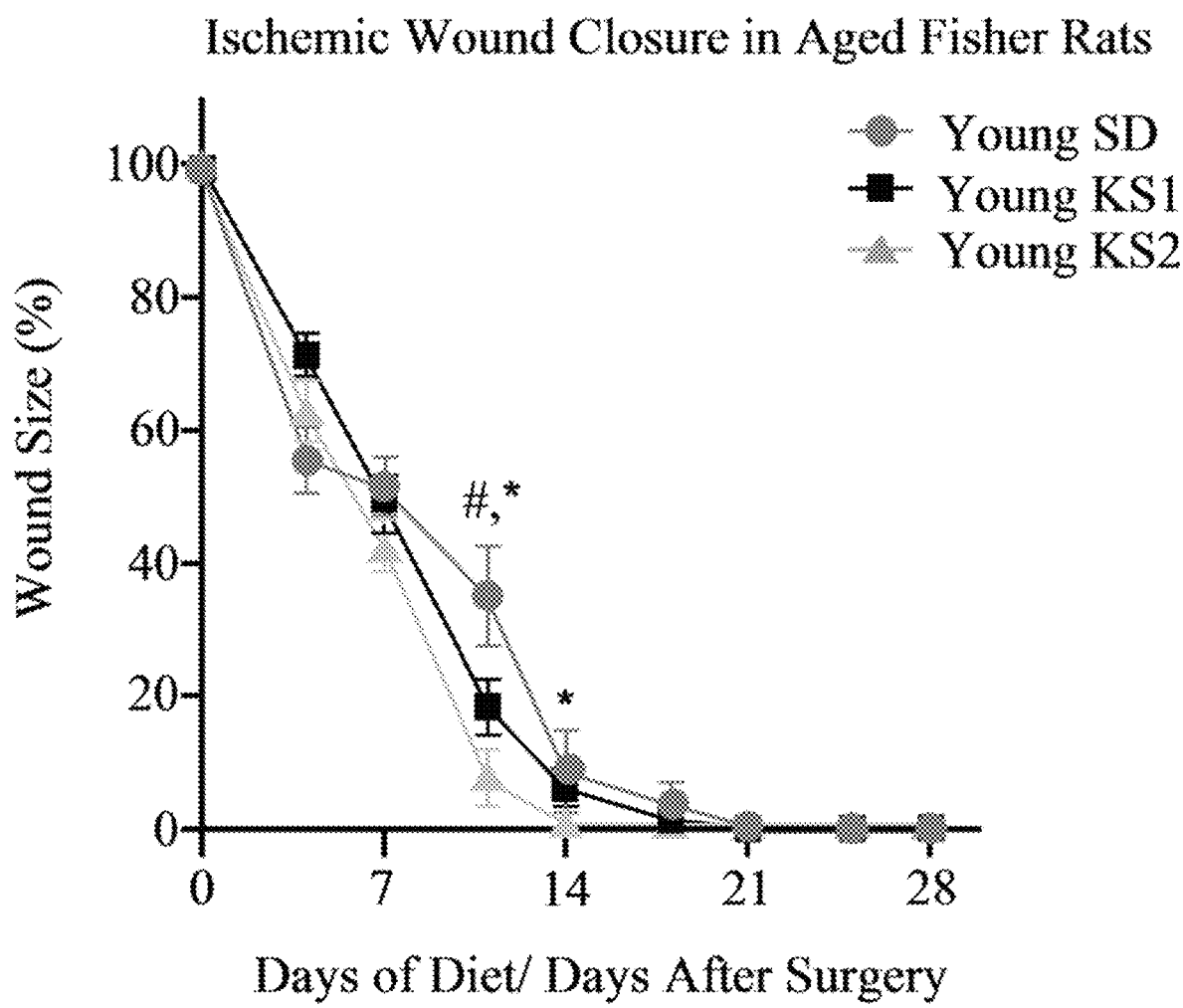
FIG. 10 is a graph showing ischemic wound healing in young Fisher rats (n=10 per group) at various days. Ketone treatments significantly decreases wound closure time by three days.
Figure 11:
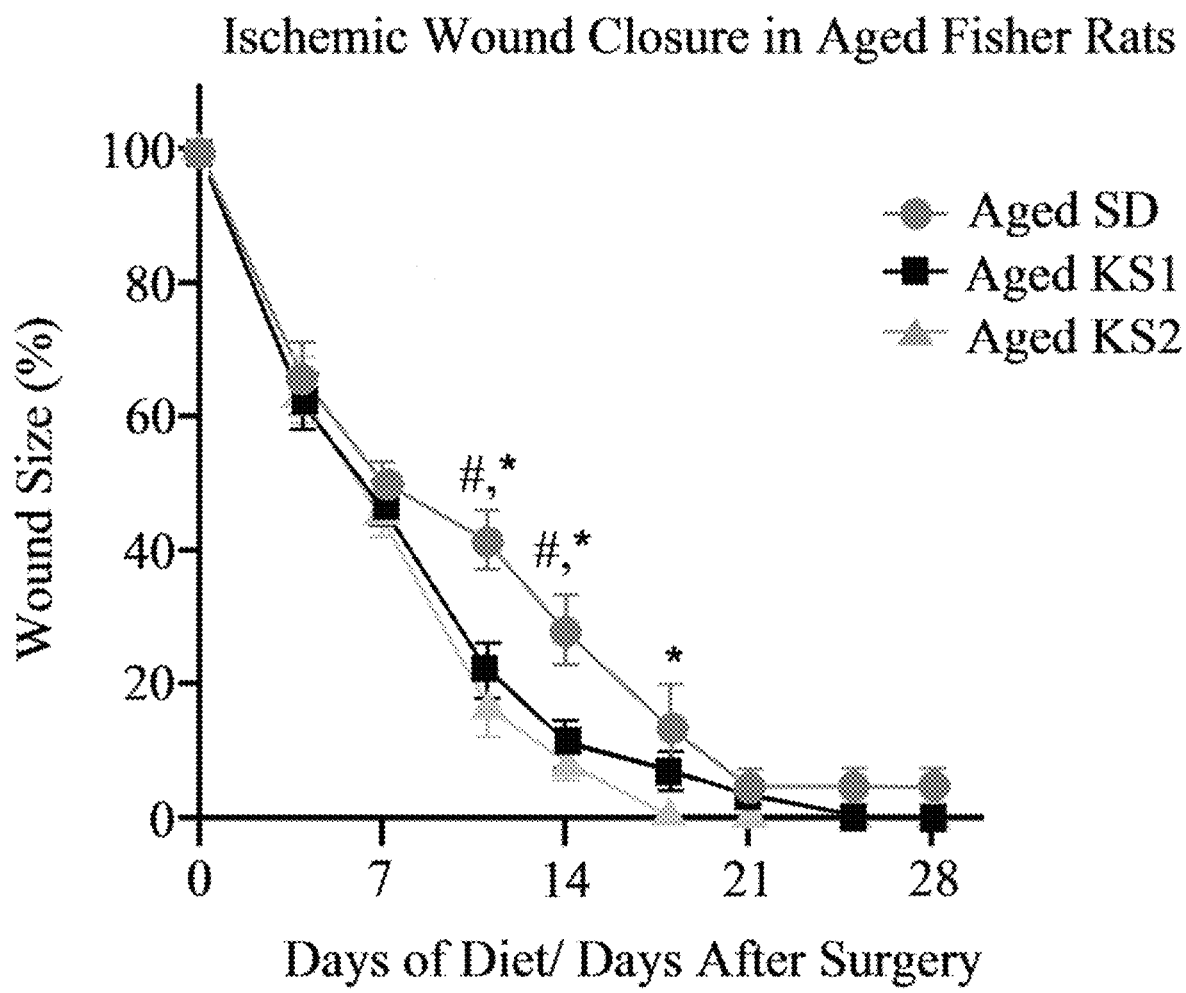
FIG. 11 is a graph showing ischemic wound healing in young Fisher rats (n=10 per group) at various days. Ketone treatments significantly decreases wound closure time by three days.

In ischemic wound repair, young Fisher rats (n=10 per group) administered ketone supplemented diets showed significant differences in wound healing (closure) rates at day 11 (p=0.0493 for KS1; p=0.0022 for KS2) compared to control. In MCT+BHB mineral salt-treated rats (KS2), this pattern continued through day 14, where the ketone supplemented diets improved wound healing (p=0.0349 for KS2), as seen in FIG. 10. In the aged Fisher rats (n=10 per group), ketone supplemented diet improved wound healing at day 11 (p=0.0230 for KS1; p=0.0115 for KS2) and 14 (p=0.0233 for KS1; p=0.0016 for KS2) compared to the control, as seen in FIG. 11. The combination treatment using MCT and BHB mineral salts (KS2) further improved wound healing through day 28 (p=00010), as seen in FIG. 11.

Example 3

To determine the time course of ketosis, a 100 kg male human was orally given the test substances of a BHB salt solution containing 4% Na$^+$/K$^+$ BHB salts (450 mL; 4%, approximately 18 g), an MCT oil (30 mL, approximately 30 g), or a combination of the a BHB salt solution and an MCT oil. Blood concentrations of glucose and BHB were determined utilizing a commercially available glucose/ketone monitoring system (Precision Xtra® blood glucose and ketone meter) at defined time points. At 0, 15, 30, 60, 120, 240 and 480 minutes following ingestion of the test substances, blood was drawn. The tests were repeated on days 2 and 3 with the same individual, using a daily additional supplement, with blood taken as on day 1. Levels of BHB in the blood were determined as described above. Administration of the Na$^+$/K$^+$ BHB salt solution showed that plasma levels of BHB peaked at 30 to 60 minutes after administration, as seen in Table 1.

TABLE 1

Blood BHB levels (mmol/L) of a 100 kg male subject following a single daily of oral administration of either BHB salts (4% solution containing 11 grams sodium BHB and 7.1 grams potassium BHB), 30 mL of MCT oil or 11.1 g of BHB salts + 20 mL of MCT oil at 15, 30, 60, 120, 240 and 480 minutes on three consecutive days.

| Supplementation | Time Min | Day 1 mM | Day 2 mM | Day 3 mM | Mean mM |
|---|---|---|---|---|---|
| BHB salt (450 mL) | 0 | 0.2 | 0.4 | 0.1 | 0.23 |
| | 15 | 0.5 | 0.8 | 0.8 | 0.70 |
| | 30 | 0.8 | 0.8 | 1.2 | 0.93 |
| | 60 | 1 | 0.6 | 1.2 | 0.93 |
| | 120 | 1.2 | 0.3 | 0.8 | 0.77 |
| | 240 | 0.4 | 0.1 | 0.3 | 0.27 |
| | 480 | 0.3 | 0.2 | 0.3 | 0.27 |
| MCT (30 mL) | 0 | 0.1 | 0.3 | 0.2 | 0.20 |
| | 15 | 0.2 | 0.3 | 0.4 | 0.30 |
| | 30 | 0.4 | 0.8 | 0.4 | 0.53 |
| | 60 | 0.5 | 0.6 | 0.5 | 0.53 |
| | 120 | 0.5 | 0.6 | 0.3 | 0.47 |
| | 240 | 0.1 | 0.2 | 0.1 | 0.13 |
| | 480 | 0.2 | 0.1 | 0.1 | 0.13 |
| BHB salt (450 mL) + MCT (30 mL) | 0 | 0.1 | 0.3 | 0.2 | 0.20 |
| | 15 | 0.5 | 0.7 | 0.4 | 0.53 |
| | 30 | 0.7 | 0.8 | 1.0 | 0.83 |
| | 60 | 1.3 | 1.2 | 1.5 | 1.33 |
| | 120 | 0.9 | 1.2 | 1.2 | 1.10 |
| | 240 | 0.4 | 1.0 | 0.5 | 0.63 |
| | 480 | 0.4 | 0.8 | 0.3 | 0.50 |

Administration of MCT oil showed little elevation in BHB levels. Administration of BHB salts showed higher elevation in BHB levels than MCT oil alone. The combination of BHB salts showed further elevation in BHB levels than either BHB salts or MCT oils alone. In comparison, administration of Na$^+$/K$^+$ BHB salt solution or the MCT oil alone showed peak BHB levels at 60 minutes, which remained fairly elevated through 120 minutes after administration, as seen in Tables 1 and 2. Further, administration the combination of Na$^+$/K$^+$ BHB salt solution and MCT oil increased BHB plasma levels well above those seen by BHB salts or MCT oil alone, as evidence of a synergistic effect between the combination of Na$^+$/K$^+$ BHB salt and MCT oil. By day 3, administration of the combination of MCT and Na$^+$/K$^+$ BHB salt solution resulted in elevated and sustained BHB plasma levels after the oral supplementation past the 120 minute time point.

TABLE 2

Mean blood BHB levels (mmol/L) of a 100 kg male subject over 3 days following a single daily oral administration of either BHB salts (4% solution containing 11 grams sodium BHB and 7.1 grams potassium BHB), MCT oil or BHB salts + MCT oil at 15, 30, 60, 120, 240 and 480 minutes. MCT oil uses a 1:1 ration of C8:C10.

| Hour | 4% BHB salt solution (450 mL) | MCT (30 mL) | 4% BHB salt solution (450 mL) + MCT (30 mL) |
|---|---|---|---|
| 0 | 0.23 | 0.20 | 0.20 |
| 15 | 0.70 | 0.30 | 0.53 |
| 30 | 0.93 | 0.53 | 0.83 |
| 60 | 0.93 | 0.53 | 1.33 |
| 120 | 0.77 | 0.47 | 1.10 |
| 240 | 0.27 | 0.13 | 0.63 |
| 480 | 0.27 | 0.13 | 0.50 |

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of the method of improving wound healing, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of improving wound healing, comprising:
   orally, intragastrically, intraarterially, or intravenously administering at least one ketone source to a patient, in need thereof wherein the at least one ketone source includes 1,3-butanediol and is administered to obtain ketosis in the patient;
   wherein the patient has a wound, and
   wherein the patient is fed ad libitum and is not on a ketogenic diet.

2. The method of claim 1, wherein the at least one ketone source further comprises beta-hydroxybutyrate precursor, acetoacetate, acetoacetate precursor, or at least one medium chain triglycerides or beta-hydroxybutyrate mineral salt.

3. The method of claim 2, wherein the beta-hydroxybutyrate precursor is a beta-hydroxybutyrate salt.

4. The method of claim 3, wherein the beta-hydroxybutyrate salt is sodium beta-hydroxybutyrate, arginine beta-hydroxybutyrate, potassium beta-hydroxybutyrate, calcium beta-hydroxybutyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, beta-hydroxy butyrate sodium salt, beta-hydroxy butyrate potassium salt, beta-hydroxy butyrate calcium salt, beta-hydroxy butyrate magnesium salt, or a combination thereof.

5. The method of claim 4, wherein the at least one ketone source is a racemic DL-beta hydroxybutyrate precursor or a single isomer R-beta hydroxybutyrate precursor.

6. The method of claim 2, wherein the β-hydroxybutyrate precursor is ethyl acetoacetate or ethyl beta-hydroxybutyrate.

7. The method of claim 2, wherein the β-hydroxybutyrate precursor is administered at between 2 grams and 50 grams.

8. The method of claim 1, wherein the at least one ketone source is administered at about 1 g/kg/day to about 10 g/kg/day.

9. The method of claim 2, wherein the at least one medium chain triglyceride is coconut oil, coconut milk powder, fractionated coconut oil, palm oil, palm kernel oil, caprylic acid, isolated hexanoic acid, isolated octanoic acid, isolated decanoic acid, esterified ester derivatives thereof, ethoxylated derivatives thereof, enone-ylated derivatives thereof, aldehyde derivatives thereof, monoglyceride derivatives thereof, diglyceride derivatives thereof, and triglyceride derivatives thereof, salt derivatives thereof, or a combination thereof.

10. The method of claim 9, wherein the at least one medium chain triglyceride is optionally administered at between 5 grams and 50 grams.

11. A method of reducing or treating redox stress in wound repair, comprising:
orally, intragastrically, intraarterially, or intravenously administering at least one ketone source to a patient, in need thereof wherein the at least one ketone source includes 1,3-butanediol and is administered to obtain ketosis in the patient;
wherein the patient has a wound, and
wherein the patient is fed ad libitum and is not on a ketogenic diet.

12. The method of claim 11, wherein the ketone source further comprises beta-hydroxybutyrate precursor, acetoacetate, acetoacetate precursor, or at least one medium chain triglycerides or beta-hydroxybutyrate mineral salt.

13. The method of claim 12, wherein the beta-hydroxybutyrate precursor is a beta-hydroxybutyrate salt.

14. The method of claim 13, wherein the beta-hydroxybutyrate salt is sodium beta-hydroxybutyrate, arginine beta-hydroxybutyrate, potassium beta-hydroxybutyrate, calcium beta-hydroxy butyrate, magnesium beta-hydroxybutyrate, lithium beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, citrulline beta-hydroxybutyrate, beta-hydroxy butyrate sodium salt, beta-hydroxy butyrate potassium salt, beta-hydroxy butyrate calcium salt, beta-hydroxy butyrate magnesium salt, or a combination thereof.

15. The method of claim 11, wherein the ketone source further comprises a racemic DL-beta hydroxybutyrate precursor or a single isomer R-beta hydroxybutyrate precursor.

16. The method of claim 12, wherein the β-hydroxybutyrate precursor is ethyl acetoacetate, or ethyl beta-hydroxybutyrate.

17. The method of claim 12, wherein the β-hydroxybutyrate precursor is administered at between 2 grams and 50 grams.

18. The method of claim 11, wherein the ketone source is administered at about 1 g/kg/day to about 10 g/kg/day.

19. The method of claim 12, wherein the at least one medium chain triglyceride is coconut oil, coconut milk powder, fractionated coconut oil, palm oil, palm kernel oil, caprilic acid, isolated hexanoic acid, isolated octanoic acid, isolated decanoic acid, esterified ester derivatives thereof, ethoxylated derivatives thereof, enone-ylated derivatives thereof, aldehyde derivatives thereof, monoglyceride derivatives thereof, diglyceride derivatives thereof, and triglyceride derivatives thereof, salt derivatives thereof, or a combination thereof.

20. The method of claim 12, wherein the at least one medium chain triglyceride is optionally administered at between 5 grams and 50 grams.

* * * * *